United States Patent [19]

Barzaghi

[11] Patent Number: 5,256,737
[45] Date of Patent: Oct. 26, 1993

[54] THICKENING AGENTS, PROCESSES FOR THE PREPARATION THEREOF AND USE THEREOF

[75] Inventor: Massimo Barzaghi, Bergamo, Italy

[73] Assignee: Sigma Prodotti Chimici S.p.A., Bergamo, Italy

[21] Appl. No.: 784,683

[22] Filed: Oct. 29, 1991

Related U.S. Application Data

[63] Continuation of Ser. No. 578,689, Sep. 7, 1990, abandoned.

[30] Foreign Application Priority Data

Mar. 5, 1990 [IT] Italy ................................ 19565 A/90

[51] Int. Cl.$^5$ .......................... C08F 16/12; C08F 8/12
[52] U.S. Cl. .............................. 525/328.9; 525/329.5; 525/329.9; 525/330.2; 525/330.5; 525/330.6; 525/368; 525/369
[58] Field of Search ............ 424/78, 81, 78.37, 78.18, 424/78.27; 525/330.2, 328.9, 328.8, 336.2; 514/772.6

[56] References Cited

U.S. PATENT DOCUMENTS

| | | | |
|---|---|---|---|
| 2,798,053 | 7/1957 | Brown | 521/38 |
| 2,980,655 | 4/1961 | Glass et al. | 526/204 |
| 4,375,533 | 3/1983 | Park et al. | 526/193 |
| 4,472,376 | 9/1984 | Kamishita | 428/178 |
| 4,524,186 | 6/1985 | Nagase | 525/369 |
| 4,985,514 | 1/1991 | Kimura et al. | 526/88 |

FOREIGN PATENT DOCUMENTS

2017491 10/1979 United Kingdom.

*Primary Examiner*—Peter F. Kulkosky
*Attorney, Agent, or Firm*—Griffin, Butler, Whisenhunt & Kurtossy

[57] ABSTRACT

Solid salts of cross-linked acrylic acid polymers or copolymers with alkali or aliphatic amines, useful as thickening agents, a process for the preparation thereof and the use thereof in the chemical, pharmaceutical, cosmetic, textile, paper industries.

8 Claims, No Drawings

THICKENING AGENTS, PROCESSES FOR THE PREPARATION THEREOF AND USE THEREOF

This application is a continuation of Ser. No. 07/578,689, filed Sep. 7, 1990, now abandoned.

The invention relates to solid salts of cross-linked acrylic acid polymers or copolymers with alkali or aliphatic amines, useful as thickening agents, to a process for the preparation thereof and to the use thereof in the chemical, pharmaceutical, cosmetic, textile, paper industries.

The use of acrylic acid polymers and copolymers cross-linked with small amounts of polyfunctional unsaturated monomers, such as for instance the vinyl ethers of polyhydroxy alchols, in order to make thick, viscous and stable systems such as solutions, suspensions, dispersions, emulsions, as well as to gelify them, is already known. These acid polymers in solid form are disclosed in U.S. Pat. No. 2,798,053, U.S. Pat. No. 2,980,655 and U.S. Pat. No. 4,375,533.

The use of those polymers in the fields of paints, inks, paper, printing in general, textile, detergents, agriculture, plastic and in the alimentary, pharmaceutical and cosmetic industries is also known (EP-A-323209, EP-A-268164, DE-A-1904309 and EP-A-210130).

The practical use of said polymers asks for a series of operations making the preparation process difficult. In fact, these powdered polymers are obtained in acidic form and must be pre-dispersed in a preliminary step before the use thereof; in order to obtain an optimal dispersion, suitable stirring systems are needed as well as particular processes for the powder addition (as reported in the GC-67 circular letter of BF Goodrich Company).

These polymers in the acidic form, when dispersed, suffer from the drawback that they are not compatible with a series of polymers such as polyvinylpyrrolidone-polyvinylpyrrolidone/polyvinylacetate-dimethyldialkylammonium chloride, which can be added only after neutralization.

The described polymers always ask for a neutralization with inorganic or organic bases before their use; this operation involves difficulties in dosing the neutralizer, since the diffusion inside the polymer, forming gels and lumps, is not immediate.

All the above mentioned drawbacks result in general disadvantages due to the need of splitting the process for the production of the compositions in more steps (dispersions, neutralization), namely:
a) pre-dispersion of the acidic form of the polymer;
b) neutralization of the pre-dispersion;
c) mixing of the pre-dispersion in the compositions;
d) addition of the constituents of the composition which are not compatible with the acidic form of the acrylic polymer.

Now it has been found that the solid salts of alkali or aliphatic amines with polymers or copolymers of acrylic acid cross-linked with 0.1–5% of polyalcohols polyalkylethers, are free from the above mentioned drawbacks involved in the use f cross-linked acrylic acid polymers and copolymers in powdered and acidic form, since they may be added with no problems directly to the formulations containing the full range of ingredients.

The salified powdered form may be obtained by neutralizing the cross-linked acrylic acid polymers and copolymers dispersed in suitable solvents by means of alkali hydroxides or aliphatic amines (for example triethanolamine) and recovering the obtained salt by filtration or solvent distillation.

According to a preferred embodiment of the invention, the sodium or potassium salts are prepared in polar solvents such as lower alcohols, particularly methanol, containing the stoichiometric amount of the sodium or potassium hydroxides or the corresponding sodium or potassium alkoxides. The possibility of using polar solvents to prepare the neutralized form of acrylic thickeners is unexpected since polyacrylic acids, having a fair solubility in the above solvents, are liable to become viscous, gelifying the reaction medium itself.

According to the invention, using the salified cross-linked acrylic acid polymers or copolymers in powdered form, it is possible to add directly the product to the mixtures to be prepared, with no need for pre-dispersion or multi-step production processes; moreover, the use of particular stirring systems is avoided since the salified polymer or co-polymer in powdered form can be dispersed without stirring in short time.

Further, according to the invention, the use of neutralizing agents is avoided and the working times are reduced, since the salified powdered polymer is dispersed much more quickly than the acidic powdered polymer; the incompatibility with some polymers is also avoided, as already specified.

The following examples illustrate the preparation of the thickeners of the invention and some comparative formulations between the method of the invention and the known method based on the use of the corresponding polymers in acidic form. Said formulations are practically used as shown in the Examples.

EXAMPLE 1

80 g of NaOH (2 moles) were dissolved in 911 ml of methanol. 200 g (2.63 moles) of a polyacrylic acid cross-linked with 0.9% of pentaerythritol triallylether having mean molecular weight of $2.5.10^6$ were added portionwise under stirring and cooling. The mixture was stirred for 30 minutes, filtered and dried to obtain 244 g of a white flowable powder consisting of the sodium salt of the used acid.

EXAMPLE 2

46 g of sodium (2 moles) were dissolved in 911 ml of methanol obtaining a 4.9% w/v sodium methoxide solution. 200 g of a polyacrylic acid cross-linked with 0.5% of sorbitol hexaallylether, having a mean molecular weight of 2.105, were added to said solution which was stirred for 30 minutes and then evaporated to dryness to obtain 244 g of the sodium salt of the used acid.

EXAMPLE 3

112 g of KOH (2 moles) were dissolved in 890 ml of ethanol. 200 g of a polyacrylic acid cross-linked with 2% of pentaerythritol triallylether having mean molecular weight of $4.10^6$ were added portionwise under stirring. The mixture was evaporated to dryness obtaining 276 g of the potassium salt of the used acid.

| FORMULATION 1 (Hair-conditioning gel) | |
|---|---|
| Formulation A | |
| Phase 1 | |
| Water | to 100 |
| Polyacrylic acid cross-linked | 0.5 |

FORMULATION 1
(Hair-conditioning gel)

| | |
|---|---|
| with 1.15% of pentaerythritol triallylether | |
| Phase 2 | |
| 95% Alcohol | 15 |
| Glycerin | 5 |
| Imidazolidinyl urea | 0.3 |
| Methyl paraoxybenzoate | 0.1 |
| Water | 20 |
| Color/perfume | q.s. |
| Phase 3 | |
| Water | 10 |
| Dimethyldiallylammonium chloride | 1 |
| Sodium hydroxide | 0.2 |
| Formulation B | |
| Water | to 100 |
| 95% Alcohol | 15 |
| Glycerin | 5 |
| Imidazolidinyl urea | 0.3 |
| Methyl paraoxybenzoate | 0.1 |
| Dimethyldiallylammonium chloride | 1 |
| Color/perfume | 0.5 |
| Polyacrylic acid cross-linked with polyfunctional agents, salified according to the invention | |

The preparation of formulation A, containing a conventional cross-linked polyacrylic acid, required the dispersion of phase 1, which took three hours; phase 2 was then added to phase 1 and then phase 3 to the other two. After the formulation was completed, stirring was continued for 30 minutes for a convenient homogenization.

Three different reactors were used and stirring was carried out by means of a turbo-emulsifier to disperse phase 1, due to the high concentration of polymer in this phase.

For the preparation of formulation B, the solid salt of a cross-linked polyacrylic acid was used, using a normal propeller stirrer and adding the ingredients in the order of the recipe into a single reactor.

A product having the same characteristics of formulation A was obtained in about 30 minutes from the addition of the last ingredient.

FORMULATION 2
(Skin hydrating emulsion)

Formulation A

| | |
|---|---|
| Phase 1 | |
| Water | to 100 |
| Polyacrylic acid cross-linked with 0.3% of pentaerythritol triallylether | 0.5 |
| Phase 2 | |
| Propylene glycol | 5 |
| Imidazolidinylurea | 0.3 |
| Methyl paraoxybenzoate | 0.05 |
| Phase 3 | |
| Caprilyc/caprinic triglyceride | 7 |
| Cetylstearyl octanoate | 7 |
| Cetyl alcohol | 3 |
| Lanoline | 0.5 |
| Sorbitan EO (20) monostearate | 3 |
| Propyl paraoxybenzoate | 0.05 |
| Phase 4 | |
| Water | 10 |
| Sodium hydroxide | 0.2 |
| Formulation B | |
| Phase 1 | |
| Water | to 100 |
| Propylene glycol | 5 |

FORMULATION 2
(Skin hydrating emulsion)

| | |
|---|---|
| Imidazolidinylurea | 0.3 |
| Methyl paraoxybenzoate | 0.05 |
| Phase 2 | |
| Caprilyc/caprinic triglyceride | 7 |
| Cetylstearyl octanoate | 7 |
| Octyldodecanol | 5 |
| Cetyl alcohol | 3 |
| Lanoline | 0.5 |
| Sorbitan OE (20) monostearate | 3 |
| Propyl paraoxybenzoate | 0.05 |
| Polyacrylic acid cross-linked with polyfunctional agents, salified according to the invention | 0.5 |

The preparation of formulation A required the dispersion of the polymer in water of phase 1 and this step took about 2 hours. Phase 2 was added to phase 1, heating to 70° C.

Phase 3, heated to 70° C., was added to the other two phases.

Finally, during cooling, phase 4 was added and stirring was continued until complete cooling. Four reactors were used for the preparation of formulation A.

For the preparation of formulation B, phases 1 and 2, heated to 70° C., were separately dispersed and added to each other under stirring. Upon homogenization of the phases, the salified polyacrylic acid in powdered form was added and cooling was started.

The emulsion was cooled in about 30 minutes with the contemporaneous complete dispersion of the polymer. In this case, the production steps were practically reduced to two and the time normally required for cooling was sufficient to disperse the salified polymer.

FORMULATION 3
(Anti-dandruff shampoo)

Formulation A

| | |
|---|---|
| Phase 1 | |
| Water | to 100 |
| Polyacrylic acid cross-linked with 2.2% of triallylether pentaerythritol | 0.5 |
| Phase 2 | |
| Water | 30 |
| Coccoylamido propylbetaine | 10 |
| Lauroyl diethanolamide | 2.5 |
| Cetylstearyl alcohol 20 (OE) | 2 |
| Sodium lauryl ether sulfate | 4 |
| Phase 3 | |
| Zinc pyridinethione | 2 |
| Phase 4 | |
| Water | 10 |
| Dimethyldiallylammonium chloride | 3 |
| Sodium hydroxide | 0.2 |
| Formulation B | |
| Phase 1 | |
| Water | to 100 |
| Coccoylamido propylbetaine | 10 |
| Lauroyl diethanolamide | 2.5 |
| Cetylstearyl alcohol 20 (OE) | 2 |
| Sodium laurylether sulfate | 4 |
| Dimethyldiallylammonium chloride | 3 |
| Zinc pyridinethione | 2 |
| Sodium salt of polyacrylic acid cross-linked with polyfunctional agents according to the invention | 0.5 |

Formulation A was prepared with a multi-step process comprising the dispersion of the cross-linked polyacrylic acid in acid form, due to the necessity of mixing the predispersed polymer with surfactants and then incorporating the quaternary polymer incompatible with the acrylic acid polymer.

The production time was determined both by the dispersion time of phase A, about 2 hours, and by the time necessary for a complete neutralization.

Formulation B was prepared in a single step by addition of the salified cross-linked polyacrylic acid in powdered form after all the other ingredients and continuing stirring for about 30 minutes obtaining the same results as for formulation A.

I claim:

1. A process for the neutralization of a free acid form of cross-linked polymers or copolymers of acrylic acid so as to obtain the corresponding salts, comprising:
   (1) preparing a solution or dispersion of a neutralizing agent consisting of sodium hydroxide in methanol, sodium in methanol or potassium hydroxide in ethanol;
   (2) adding to the neutralizing agent with mixing the free acid form of the polymers or copolymers or acrylic acid to form the solid salts thereof; and
   (3) recovering the salts by filtration or evaporation as a free-flowing powder.

2. The process of claim 1 wherein the neutralizing agent is sodium hydroxide in methanol.

3. The process of claim 1 wherein the neutralizing agent is in about stoichiometric amounts.

4. The process of claim 1 wherein the polymers or copolymers of acrylic acid are cross-linked with 0.1–5% of polyalcohol polyallylethers.

5. The process of claim 4 wherein the polyalcohol polyallylethers are pentaerythritol or sorbitol polyallylether.

6. The process of claim 1 wherein the cross-linked polymer is polyacrylic acid cross-linked with pentaerythritol triallylether.

7. The product produced by the process of claim 1.

8. The process of claim 1 wherein the cross-linked polymers or copolymers of acrylic acid have a molecular weight ranging from $5.10^4$ to $5.10^6$.

* * * * *